(12) United States Patent
Venturi et al.

(10) Patent No.: US 8,754,239 B2
(45) Date of Patent: Jun. 17, 2014

(54) PROCESS FOR PREPARING ELETRIPTAN HYDROBROMIDE HAVING α-FORM

(75) Inventors: Srinivasa Rao Venturi, Hyderabad (IN); Hari Prasad Kodali, Hyderabad (IN); Hariharakrishnan Venkata Subhramanian, Hyderabad (IN); Venkata Srihari Tadimalla, Hyderabad (IN); Ramesh Babu Potluri, Hyderabad (IN)

(73) Assignee: SMS Pharmaceuticals Limited (IN)

( * ) Notice: Subject to any disclaimer, the term of this patent is extended or adjusted under 35 U.S.C. 154(b) by 0 days.

(21) Appl. No.: 13/522,850

(22) PCT Filed: Mar. 31, 2010

(86) PCT No.: PCT/IN2010/000212
§ 371 (c)(1),
(2), (4) Date: Oct. 8, 2012

(87) PCT Pub. No.: WO2011/089614
PCT Pub. Date: Jul. 28, 2011

(65) Prior Publication Data
US 2013/0023672 A1 Jan. 24, 2013

(30) Foreign Application Priority Data
Jan. 19, 2010 (IN) .............................. 131/CHE/2010

(51) Int. Cl.
*C07D 403/06* (2006.01)
(52) U.S. Cl.
USPC ....................................................... 548/468
(58) Field of Classification Search
USPC ....................................................... 548/468
See application file for complete search history.

(56) References Cited

U.S. PATENT DOCUMENTS

| | | | |
|---|---|---|---|
| 5,545,644 | A | 8/1996 | Macor et al. |
| 5,607,951 | A | 3/1997 | Macor et al. |
| 5,639,779 | A | 6/1997 | Wythes et al. |
| 6,927,296 | B2 | 8/2005 | Furlong et al. |
| 2002/0013358 | A1 * | 1/2002 | Dallmann et al. ............ 514/415 |
| 2003/0166704 | A1 | 9/2003 | Ogilvie |

FOREIGN PATENT DOCUMENTS

| | | |
|---|---|---|
| EP | 1088817 | 4/2001 |
| WO | 9206973 | 4/1992 |
| WO | 9606842 | 3/1996 |
| WO | 0032589 | 6/2000 |
| WO | 0250063 | 6/2002 |
| WO | 2005007649 | 1/2005 |

OTHER PUBLICATIONS

International Search Report for PCT App. No. PCT/IN2010/000212 mailed on Nov. 11, 2010.

* cited by examiner

*Primary Examiner* — Shawquia Young
(74) *Attorney, Agent, or Firm* — Whyte Hirschboeck Dudek S.C.

(57) ABSTRACT

A process for preparation of eletriptan hydrobromide having α-form of formula (I) is described that includes reducing 3-((R)-1-methylpyrrolidin-2-yl)methyl)-5-((E)-2-(phenylsulfonyl)vinyl)-1H-indole of formula (II) in presence of a metal catalyst to the product of formula (III) and then converting to hydrobromide salt having α-form of formula (I).

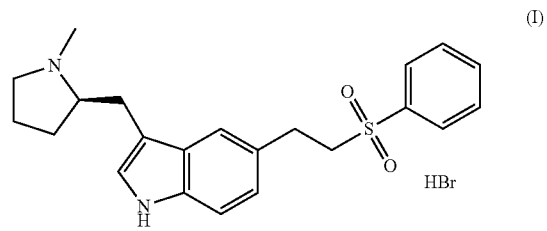

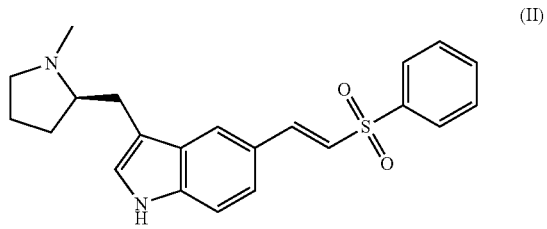

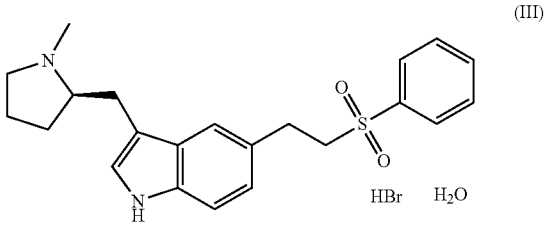

11 Claims, 2 Drawing Sheets

Figure 1:
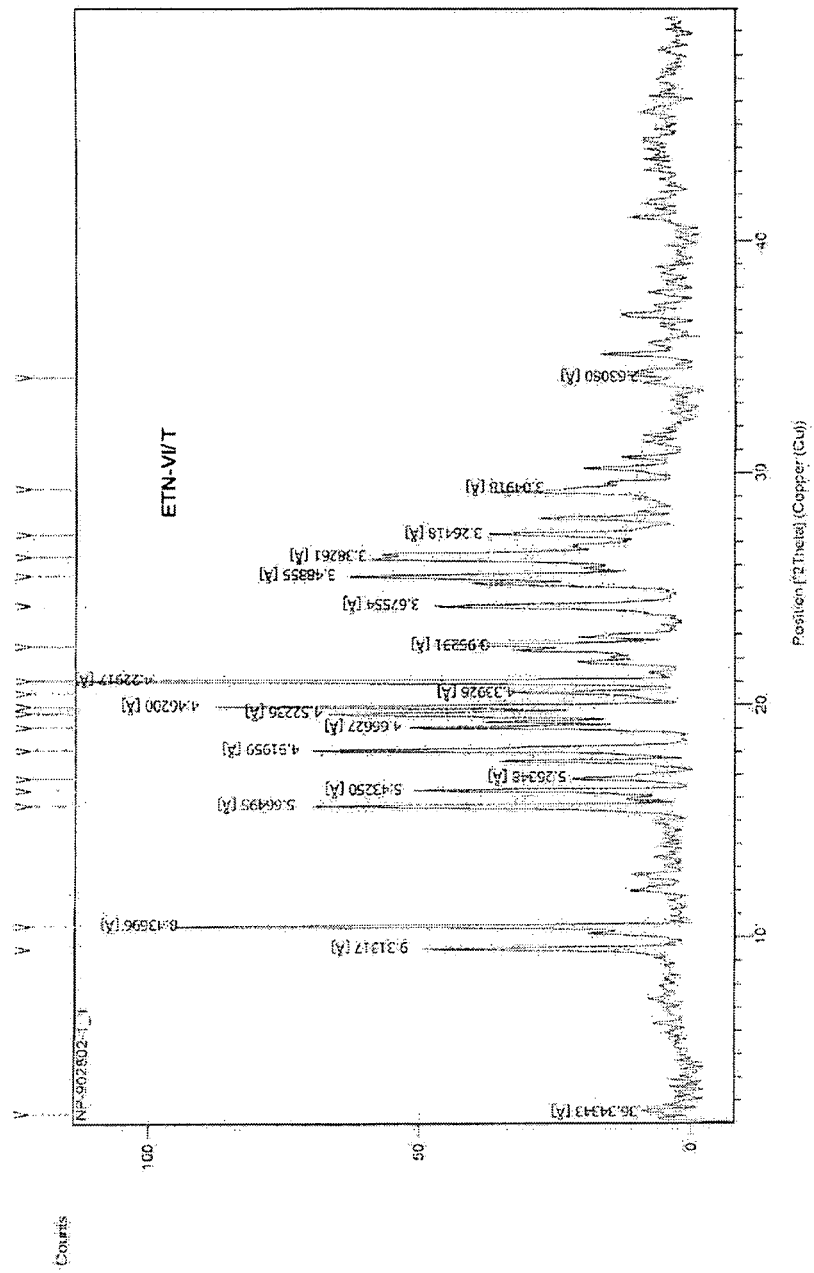

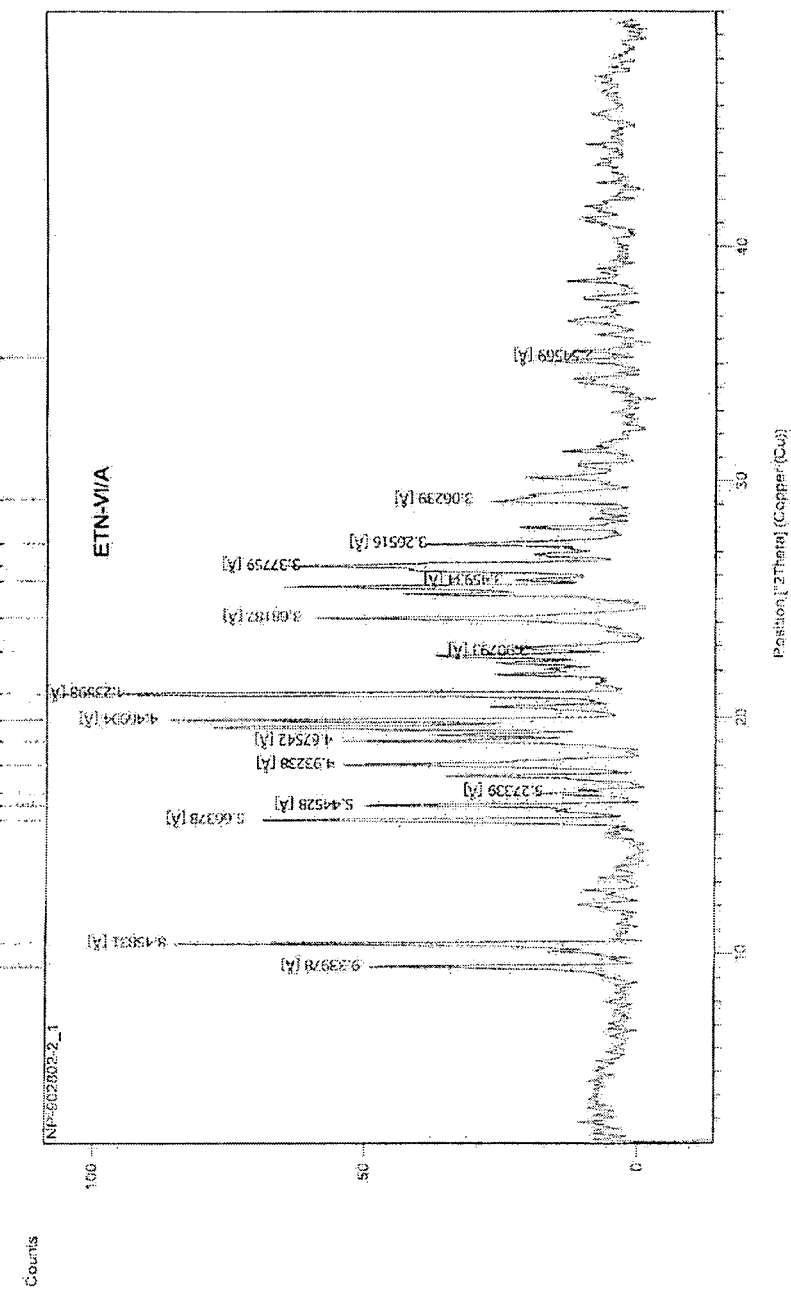
FIG-II

PROCESS FOR PREPARING ELETRIPTAN HYDROBROMIDE HAVING α-FORM

BACK GROUND OF THE INVENTION

This invention relates to an economical process for preparation of eletriptan hydrobromide α-form of formula-I and its monohydrate of formula-III by the hydrogenation of the precursor of formula-II.

The invention also describes a method for achieving to get α-polymorphic crystalline from of eletriptan hydrobromide α-form of formula-I Eletriptan, 3-(((R)-1-methylpyrrolidin-2-yl)methyl)-5-(2-(phenyl sulfonyl)ethyl)-1H-indole, is described in U.S. Pat. No. 5,607,951 (WO1992/06973). Process for this product is reported in EP1088817, as well as, WO/2002/50063.

Conversion of the product of formula-II to the product of formula-III is carried out by catalytic hydrogenation in the presence of an acid using Pd/C as catalyst.

U.S. Pat. No. 5,545,644 describes indole derivatives including Eletriptan. The patent gives a method for their preparation, where the hydrogenation is carried out using Pd/C in the presence of methane sulfonic acid.

A similar method is described in U.S. Pat. No. 5,639,779.

PCT WO/2002/50063A1 has also reported Pd/C catalyzed hydrogenation of a double bond. The substrate used is N-acetyl derivative of the product formula-II. The N-acetyl derivative of the product of formula-II is used in order to control the formation of the of bisindole derivative.

US Patent 2003/016074A1 undertakes the hydrogenation of the product of formula-II as acetyl derivative using Pd/C, PtO₂, Ru, Rh or Raney-Ni.

Several patents describe the preparation of α-polymorphic form of eletriptan hydrobromide WO1996/06842 A and WO2000/32589A claim the preparation of α-polymorph. In WO2000/32589A describe two methods, a) treating eletriptan base with acetone and aqueous hydrobromic acid and slurrying the oil formed in isopropyl alcohol, b) treating eletriptan base with acetone containing aqueous hydrobromic acid, refluxing and slurrying a second time in acetone.

U.S. Pat. No. 6,927,296 B2 describes α-polymorphic form using 2-butanone and aqueous hydrobromic acid. The mixture is subjected to azeotropic distillation along with toluene.

The conversion of the product of formula-II to the product of formula-I has been described in several aforementioned patents.

Analysis of these patents expose a few shortcomings. These are as given below
  a) The process is successful most preferably with Pd/C and the catalyst is used in more quantities making the process uneconomical
  b) The process is effective in the presence of an acid, preferably methane sulfonic acid and this makes it an environmental load.
  c) Hydrogenation of N-acetyl derivative of the product of formula-II to the product of formula-I has been claimed using Raney Nickel in US Patent 2003/016674A1. It is observed that this reaction gives the indole derivative of formula-IV as an impurity. Additionally it requires another step of deacetylation

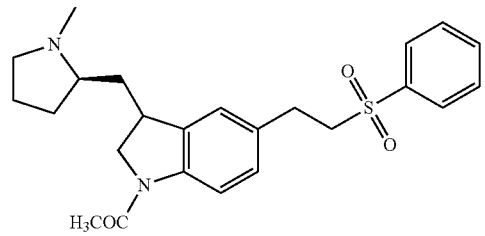

Formula-IV d) Scale up by the methods mentioned herein gives an overall yield of 73%

SUMMARY OF INVENTION

The objective of the invention is to develop an economical method for the conversion of the product of formula-II to the product of formula-III and its conversion to hydrobromide salt α-form of the product of formula-I Considering that conversion of the product of formula-II to the product of formula-III has been achieved by using Raney Nickel as catalyst.

The product of formula-III has been converted to the product of formula-I

DETAILED DESCRIPTION OF THE INVENTION

The main objective of the invention is to develop an economical method for the synthesis for Eletriptan hydrobromide α-form of formula-I.

It is an objective of the invention to use an economically viable catalyst for the hydrogenation of the product of formula-II to the product of formula-III It is another objective to carry out an environmentally friendly conditions.

It is yet another objective to convert the product of formula-III to formula-I in an economical fashion.

The objective has been achieved by the hydrogenation of the product of formula-II

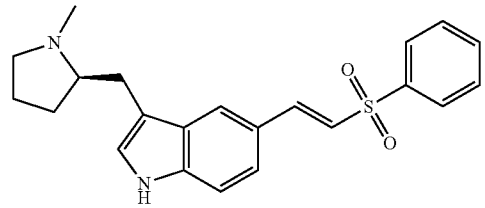

Formula-II to the product of formula-III

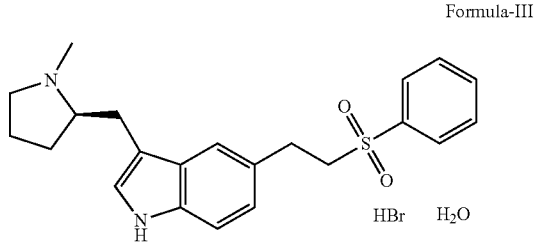 [SMILES: CN1CCC[C@@H]1Cc1c[nH]c2ccc(CCS(=O)(=O)c3ccccc3)cc12 ; Br ; O]

Formula-III by conducting the hydrogenation using catalysts like Pd/C, PtO₂ or Raney Nickel in the absence of an acid in a solvent selected from the group consisting of methanol, ethanol, isopropanol, n-butanol, acetone, methylethylketone, ethyl acetate, acetonitrile or N,N-dimethylformamide either alone or as a mixture of any of two solvent and converting the product formula-III to the product of formula-I

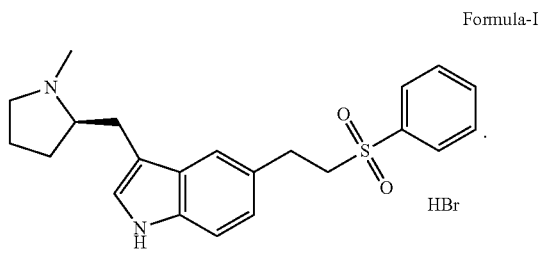 [SMILES: CN1CCC[C@@H]1Cc1c[nH]c2ccc(CCS(=O)(=O)c3ccccc3)cc12 ; Br]

Formula-I by treating of the product of formula-III in a solvent selected from the group acetone, methylethylketone, isopropyl alcohol, toluene or n-butanol, preferably a ketonic solvent in 95% yield and >99.7% HPLC purity.

The invention has achieved the preparation of α-polymorph of the product of formula-I The conversion of the product of formula-II to the product of formula-III was attempted using the catalysts selected from the group consisting of Pd/C, PtO₂, Rh, Ru and Raney Ni in solvent selected from the group consisting of methanol, ethanol, isopropanol, n-butanol, acetone, methylethylketone, ethyl acetate, acetonitrile or N,N-dimethylformamide either alone or as a mixture of any of the two solvents. Hydrogenation was tried in the presence of an acid selected from hydrochloric acid, sulphuric acid, phosphoric acid or methanesulfonic acid. Reaction was taking place smoothly in the presence of an acid, preferably methane sulfonic acid. In the absence of an acid, the reaction was sluggish and incomplete. Studies revealed that the preferred catalyst is Pd/C and the catalyst is Pd/C and the catalyst has to be used in higher performance in order to achieve a smooth process, catalyst was used in 30-50% w/w. This process hence, becomes, economically unfavorable.

Hence further studies for hydrogenation were carried out using Raney Nickel as catalyst without using an acid.

Hydrogenation was carried out in a solvent selected from an alkanol consisting methanol, ethanol, isopropanol, n-butanol, acetone, methylethylketone, ethyl acetate, acetonitrile or N,N-dimethylformamide.

Preferably hydrogenation is conducted in a solvent selected from the group consisting of methyl alcohol, isopropyl alcohol, acetone or methylethylketone.

Raney Nickel was used a catalyst in 5% to 30% and preferably in 10% to 20%. Hydrogenation was conducted preferably at 10 to 90° C. for 2 to 10 hours and more preferably at 25 to 75° C. for 4 to 6 hours.

Isolation of the product of formula-III in a solvent selected from the group consisting of isopropyl alcohol, acetone, ethyl acetate or methylethylketone containing 48% aqueous hydrobromic acid. This isolation method eliminated small quantities of bis impurity.

The product of formula-III was isolated in 90-95% yield with a melting range of 115-119° C. and HPLC purity of >99%.

The product of formula-III was treated in a solvent selected from the group consisting of isopropyl alcohol, n-butyl alcohol, t-butyl alcohol, acetone, toluene along or a mixture of any of the two solvents.

The treatment was carried out at 50-120° C., preferably 60-100° C. and isolated as anhydrous eletriptan hydrobromide in α-polymorphic form. The α-polymorph was isolation in 85-90% yield having a melting range of 160-170° C.

This polymorph has XRD values as 9.49, 10.48, 15.64, 16.31, 16.84, 18.03, 19.01, 19.63, 19.89, 20.46, 21.00, 22.49, 24.21, 25.53, 26.34, 27.32 and 29.29. The DSC exotherm is 169° C. The HPLC purity of the α-polymorph is 99.7%.

Thus this invention has achieved the following achievement
  a) By preferably conduction hydrogenation using Raney Nickel as catalyst, a tremendous amount of economy has been achieved.
  b) Since hydrogenation is proceeding in the absence of an acid, the process is environmentally friendly
  c) Process has achieved formation of α-polymorph of eletriptan hydrobromide with high yield and purity The following examples exemplify the invention. That should not construed in limiting the range of application of the invention Example-1

3-(((R)-1-Methylpyrrolidin-2-yl)methyl)-5-((E)-2-(phenylsulfonyl)vinyl)-1H-indole (which was prepared according to the procedure described in WO 1992/06973) 2 kg and methanol (20 L) charged into hydrogenator. Raney Nickel (0.5 kg) was added carefully under vacuum and evacuated. The reactor was applied with a hydrogen pressure of 70-75 psi. The reaction was maintained until the hydrogen consumption ceases (usually 4-5 hours). The reaction mixture was filtered and filtrate concentrated under reduced pressure. The remaining residue dissolved in ethyl acetate (10 L) and 48% aqueous hydrobromic acid (1.1 kg) added. The mixture was stirred for 30 minutes and filtered. The obtained product was dried at 45-50° C. under reduced pressure for 4-5 hours to give 2.41 kg of eletriptan hydrobromide monohydrate with a melting point of 118-119° C. and purity by HPLC 99.5%.

Example-2

Eletriptan hydrobromide monohydrate (1.0 kg) which was prepared in example-1 was charged into toluene (10 L) and refluxed for 2 hours. The reaction mass was distilled till the volumes reduced to 3 L and cooled to 25-30° C. Stir for 30 minutes and filtered off. The wet material was dried at 50-55° C. to give 0.9 kg of eletriptan hydrobromide with a melting point of 169-171° C. and purity by HPLC 99.8%. PXRD data in Fig-I shows α-polymorph Example-3

Eletriptan hydrobromide monohydrate (1.0 kg) which was prepared in example-1 was charged into isopropylalcohol (8

L) and refluxed for 2 hours. The reaction mass was distilled till the volumes reduced to 2 L and cooled to 25-30° C. Stirred for 30 minutes and filtered off. The wet material was dried at 45-50° C. to give 0.93 kg of eletriptan hydrobromide with a melting point of 168-170° C. and purity by HPLC 99.7%. PXRD data in Fig-II shows α-polymorph Example-4

Eletriptan hydrobromide monohydrate (0.4 kg) which was prepared in example-1 was charged into acetone (4 L) and refluxed for 2 hours. The reaction mass was distilled till the volumes reduced to 1.2 L and cooled to 25-30° C. Stirred for 30 minutes and filtered off. The wet material was dried at 45-50° C. to give 0.36 kg of eletriptan hydrobromide with a melting point of 169-171° C. and purity by HPLC 99.8%.

The invention claimed is:

1. A process for preparation of eletriptan hydrobromide monohydrate of formula-III which comprises: a) reducing (((R)-1-methylpyrrolidin-2-yl)methyl)-5-((E)-2-(phenylsulfonyl)-vinyl)-1H-indole of formula II

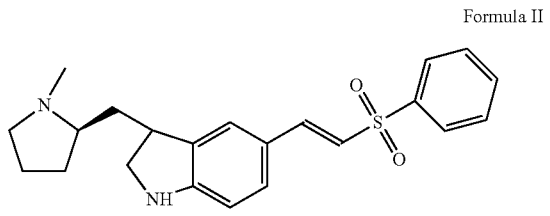 [SMILES: CN1CCC[C@@H]1CC1CNc2ccc(/C=C/S(=O)(=O)c3ccccc3)cc21]

Formula II in presence of a metal catalyst and hydrogen in an organic solvent in the absence of an acid; and b) isolating the eletriptan hydrobromide monohydrate (formula-III)

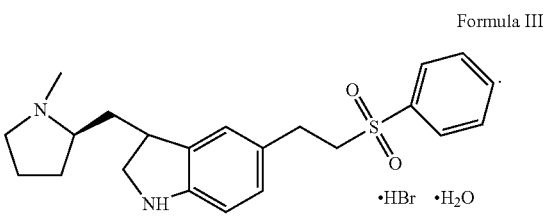

Formula III

2. A process, as claimed in claim 1, wherein the reduction is carried out using hydrogen and a metal catalyst in the absense of an acid.

3. A process, as claimed in claim 1, wherein the metal catalyst used is Raney-nickel.

4. A process, as claimed in claim 1, wherein the reduction is carried out in an alcoholic solvent selected from the group consisting of methanol, ethanol, butanol, isopropanol or ketonic solvents selected from the group consisting of acetone, methylethyl ketone, ethyl acetate, acetonitrile, dimethylformamide, either alone or a mixture of any of these solvents.

5. A process, as claimed in claim 1, wherein the reduction is carried out at 10-90° C., preferably 25-75° C.

6. A process, as claimed in claim 1, wherein eletriptan hydrobromide monohydrate is isolated in an organic solvent by adding aqueous hydrobromic acid.

7. A process for preparation of eletriptan hydrobromide α-form of formula I which comprises converting the eletriptan hydrobromide monohydrate obtained according to the process claimed in claim 1 to eletriptan hydrobromide α-form

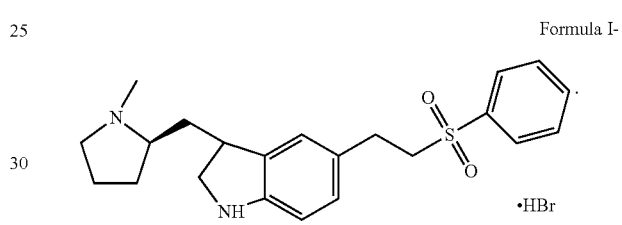

Formula I-

8. A process as claimed in claim 7, wherein eletriptan hydrobromide monohydrate is converted to eletriptan hydrobromide by refluxing in an organic solvent.

9. A process as claimed in claim 8, wherein the organic solvent used is selected from group consisting of acetone, 2-propanol, n-butanol, t-butanol, toluene either alone or a mixture of any of these solvents.

10. A process as claimed in claim 7, wherein the eletriptan hydrobromide monohydrate was refluxed, distilled, cooled and filtered to get eletriptan hydrobromide α-form.

11. A process as claimed in claim 10, wherein the reaction mixture is cooled to 0-35° C.

* * * * *